(12) United States Patent
Adamis (10) Patent No.: US 6,670,321 B1
(45) Date of Patent: Dec. 30, 2003

(54) PREVENTION AND TREATMENT FOR RETINAL ISCHEMIA AND EDEMA

(75) Inventor: Anthony P. Adamis, Jamaica Plain, MA (US)

(73) Assignee: The Children's Medical Center Corporation, Boston, MA (US)

( * ) Notice: Subject to any disclaimer, the term of this patent is extended or adjusted under 35 U.S.C. 154(b) by 0 days.

(21) Appl. No.: 09/248,752

(22) Filed: Feb. 12, 1999

Related U.S. Application Data (60) Provisional application No. 60/114,221, filed on Dec. 30, 1998.

(51) Int. Cl.$^7$ .......................... A61K 31/00; A61K 38/00
(52) U.S. Cl. ............................... 514/2; 514/44
(58) Field of Search ..................... 435/6, 7.1, 69.1, 435/91.1, 440, 325, 352, 353, 366, 368, 371, 372, 375, 320.1; 530/387.1, 388.1, 388.2; 514/44, 2; 424/130.1, 133.1, 145.1, 152.1; 536/23.1, 24.31, 24.5

(56) References Cited

U.S. PATENT DOCUMENTS

| | | |
|---|---|---|
| 5,284,931 A | 2/1994 | Springer et al. |
| 5,597,567 A | 1/1997 | Whitcup et al. .......... 424/143.1 |
| 5,814,500 A | 9/1998 | Dietz ........................ 435/455 |
| 5,821,341 A | 10/1998 | McClelland et al. ... 530/388.22 |

FOREIGN PATENT DOCUMENTS

| | | |
|---|---|---|
| EP | 0 314 863 A | 5/1989 |
| EP | 0 512 301 A1 | 11/1992 |
| EP | 0 528 931 B1 | 7/1998 |
| WO | WO 91/16927 | 11/1991 |
| WO | WO 93/06864 A | 4/1993 |
| WO | WO97/46671 | * 12/1997 |
| WO | WO 98/24797 | 6/1998 |
| WO | WO 98/46264 A | 10/1998 |
| WO | WO 99/45920 | 9/1999 |

OTHER PUBLICATIONS

Yagi et al., Diabetes, vol. 44, No. 7, pp. 744–752 (Jul. 1995).*
Hayashi et al., Int. J. Exp. Path, vol. 44, No. 7, pp. 744–752 (Dec. 1995).*
Fabien et al., Diabetes, vol. 45, No. 9, pp. 1181–1186 (Sep. 1996).*
Katz et al., Transplantation Proceedings, vol. 27, No. 6, p. 3214 (Dec. 1995).*
Limb et al., British J. of Ophthalmology, 1996, v. 80, pp. 168–173, 1996.*
Whitcup et al., Clinical Immunology and Immunopathology, vol. 67, No. 2, May 1993, pp. 143–150.*
Kleinberg et al. Am J Health–Syst Pharm, vol. 52, pp. 1323–1336, Jul. 1995.*
Branch, A.D. TIBS, vol. 23, Feb. 1998, pp. 45–50.*
Stein, C.A. Nature Biotechnology, vol. 17, Aug. 1999, pp. 751–752.*
Flanagan, W.M. et al. Nature Biotechnology, vol. 17, Jan. 1999, 48–52.*
Crooke, S.T. Chapter 1, in Antisense Research and Application, (ed. Stanley Crooke), Springer–Verlang, New York, 1998, pp. 1–50.*
Serri, O. et al., Metabolism 44 (10) (Suppl 4), pp. 83–90 (Oct. 1995).*
Robbins et al., Pathologic Basis of Disease, 2d Edition, (1979), W.B. Saunders Co., Philadelphia, pp. 284–285, Feb. 1998.*
Miller, J.W. et al., Diabetes/Metabolism Review, vol. 13, No. 1, pp. 37–50 (1997).*
Olson, J.A. et al., Diabetologia (Oct. 1997), vol. 40, pp. 1166–1171.*
Lawrence M. B. et al., "Leukocytes Roll on a Selectin at Physiologic Flow Rates: Distinction from and Prerequisite for Adhesion Through Integrins," *Cell*, vol. 65:859–873 (1991).
Arnold, T. et al., "Increased PMN Adherence on Endothelial Cells After Hypoxia: Involvement of PAF, CD18/CD11b, and ICAM–1," *American Physiological Society* C1102–1110 (1993).
Springer, T. A., "Traffic Signals for Lymphocyte Recirculation and Leukocyte Emigration: The Multistep Paradigm," *Cell*, vol. 76:301–314 (1994).
Schmidt–Schöbein, G.W., "Granulocyte Activation and Capillary Obstruction," Liepshc DW (ed): Blood Flow in Large Arteries: Applications to Atherogenesis and Clinical Medicine. Monogr Atheroscler, Basel, Karger, vol. 15:150–159 (1990).
Panès, J. et al., "Diabetes Exacerbates Inflammatory Responses to Ischemia–Reperfusion," *Circulation*, vol. 93:161–167 (1996).
Lu, M. et al., "VEGF Increases Retinal Vascular ICAM–1 Expression and Neutrophil Adhesion to Endothelial Cells," *IOVS*, vol. 39(4) (1998) (Abstract).
Limb, G. A. et al., "Evidence of Chronic Inflammation in Retina Excised After Relaxing Retinotomy for Anterior Proliferative Vitreoretinopathy," *Graefe's Arch Clin. Exp. Ophthalmol*, vol. 234:213–220 (1996).

(List continued on next page.)

*Primary Examiner*—Sean McGarry
*Assistant Examiner*—Mary M. Schmidt
(74) *Attorney, Agent, or Firm*—Hamilton, Brook, Smith & Reynolds, P.C.

(57) ABSTRACT

The claimed invention relates to methods of treating retinopathy, retinal ischemia and/or retinal edema comprising administering an integrin antagonist, a leukocyte adhesion inducing cytokine antagonist, a selectin antagonist or adhesion molecule antagonist.

27 Claims, 7 Drawing Sheets

OTHER PUBLICATIONS

Douglas, J. T. et al., "Vascular and Platelet Adhesion Molecules: E–Selectin, ICAM–1, VCAM–1, GMP–140 and Platelet Derived Growth Factor in Diabetes," (Abstract) Fibrinolysis 8 (Suppl. 1), Abstract No. 373, 1994, p. 132.

Lisby, S. et al., "Intercellular Adhesion Molecule–I (ICAM–I) Expression Correlated to Inflammation," *British Journal of Dermatology,* vol. 120:479–484 (1989).

Ashton, N. "Pathogenesis of Diabetic Retinopathy," *Diabetic Retinopathy* 85–106 (1983), ed. H.L. Little et al., N.Y. Fine–Stratton, Straton.

Chakrabarti, D. et al., "IFN–α Induces Autoimmune T Cells Through the Induction of Intracellular Adhesion Molecule–1 and B7.2," *J. of Immunol. vol.* 157:522–528 (1996).

Lampeter, E. R. et al., "Elevated Levels of Circulating Adhesion Molecules in IDDM Patients and in Subjects at Risk for IDDM," *Diabetes Vol.* 41:1668–1671 (1992).

Heidenkummer, H. et al., "Intercellular Adhesion Molecule–1 (ICAM–1) and Leukocyte Function–Associated Antigen–1 (LFA–1) Expression in Human Epiretinal Membranes," *Graefe's Arch. Clin. Exp. Ophthalmol. Vol.* 230:483–487 (1992).

Albertini, J. P. et al., "Are Soluble Adhesion Glycoproteins A Marker for Coronary Lesions in the Diabetic Patient?," (Abstract) Diabetologia 40 (Suppl. 1) A397 (1997).

Schmid–SchönBein, G.W., "The Damaging Potential of Leukocyte Activation in the Microcirculation," *Angiology—The Journal of Vascular Diseases* 45–56 (1993).

Roep, B. O. et al., "Soluble Forms of Intercellular Adhesion Molecule–1 in Insulin–Dependent Diabetes Mellitus," *The Lancet,* vol. 343:1590–1593 (1994).

Kohner, E.M. et al., *Diabetic Retinopathy* 25:1985–1102 (1975).

Schröder, S. et al., "Activated Monocytes and Granulocytes, Capillary Nonperfusion, and Neovascularization in Diabetic Retinopathy," *American Journal of Pathology,* vol. 139(1):81–100 (1991).

McLeod, S. D. et al., "Enhanced Expression of Intracellular Adhesion Molecule–1 and P–Selectin in the Diabetic Human Retina and Choroid," *American Journal of Pathology,* vol. 147(3):642–653 (1995).

Larson, R. S. et al., "Structure and Function of Leukocyte Integrins," *Immunological Reviews,+* vol. 114:181–217 (1990).

De Mesmaeker, A. et al., "Antisense Oligonucleotides," *Acc. Chem. Res.,* vol. 28:366–374 (1995).

Sweeney et al., *Genetic Engineering,* 20:143–151 (1998).

Robinson, G.S. et al., "Oligodeoxynucleotides Inhibit Retinal Neovascularization in a Murine Model of Proliferative Retinopathy," *Proc. Natl. Acad. Sci. Vol.* 93:4851–4856 (1996).

Miyamoto, K. et al., "In Vivo Demonstration of Increased Leukocyte Entrapment in Retinal Microcirculation of Diabetic Rats," *Invest. Ophthalmol. Vis. Sci.* 39(11):2190–2194 (1998).

Miyamoto K. et al., "In Vivo Quantification of Leukocyte Behavior in the Retina During Endotoxin–Induced Uveitis," *Invest. Ophthalmol. Vis. Sci.* 37(13):2708–2715 (1996).

Nishiwaki H. et al., "Visualization and Quantitative Analysis of Leukocyte Dynamics in retinal Microcirculation of Rates," *Invest. Ophthalmol. Vis. Sci.* 37(7):1341–1347 (1996).

Tilton, R.G. et al., "Prevention of Diabetic Vascular Dysfunction by Guanidines Inhibition of Nitric Oxide Synthase Versus Advanced Glycation End–Product Formation," *Diabetes* 42(2):221–232 (1993).

Tilton, R.G. et al., "Vascular Dysfunction Induced by Elevated Glucose Levels in Rats is Mediated by Vascular Endothelial Growth Factor," *J. Clin. Invest.* 99(9):2192–2202 (1997).

Hynes, R.O., "Integrins: Versatility, Modulation, and Signaling in Cell Adhesion," *Cell,* 69:11–25 (Apr. 3, 1992).

Faveeuw, C., et al., "Expression of Homing and Adhesion Molecules in Infiltrated Islets of Langerhans and Salivary Glands of Nonobese Diabetic Mice," *Journal of Immunology,* 152:5969–5978(1994).

Hunger, R.E., et al., "Inhibition of Submandibular and Lacrimal Gland Infiltration in Nonobese Diabetic Mice by Transgenic Expression of Soluble TNF–receptor p55," *J. Clin. Invest.,* 98:954–961 (1996).

Prieto, J., et al., "Induction of Intercellular Adhesion Molecule–1 (CD54) on Isolated Mouse Pancreatic β Cells by Inflammatory Cytokines," *Clinical Immunology and Immunopathology,* 65(3):247–253 (Dec., 1992).

Papaccio, G., et al., "Pancreatic duct inflammatory infiltration in the nonobese diabetic (NOD) mouse," *J. Anat.,* 185:465–470 (1994).

Guha, M., et al., "Molecular and cellular alterations in monocyte/macrophages in response to hyperglycemia and inflammatory cytokines," *Blood—Journal of the American Society of Hematology,* 90(10): Abstract No. 2882 (Nov. 15, 1997).

Yoshioka, N., et al., "PS 49 Retinopathy—Experimental and Pathogenesis," *Diabetologia—Journal of the European Association for the Study of Diabetes,* 40(1): Abstract No. 1925 (Jun. 1997).

DeSouza, C.A., et al., "Elevated levels of Circulating Cell Adhesion Molecules in Uncomplicated Essential Hypertension," *The FASEB Journal,* 11(3): Abstract No. 2696 (Feb. 28, 1997).

Vejlsgaard, G.L., et al., "Kinetics and characteristics of intercellular adhesion molecule–1 (ICAM–1) expression on keratinocytes in various inflammatory skin lesions and malignant cutaneous lymphomas," *J. Am. Acad. Dermatol.,* 20:782–790 (1989).

Olson, J. A. et al., "Soluble leukocyte adhesion molecules in diabetic retinopathy stimulate retinal capillary endothelial cell migration," *Diabetologia,* 40(10):1166–71 (Oct. 1997).

Uchio E. et al., "Suppression of experimental uveitis with monoclonal antibodies to ICAM–1 and LFA–1," *Investig. Ophthalm. Visual Sc.,* 35(5):2626–31 (Apr. 1994).

Henley W. L. et al., "Leukocyte migration inhibition in chronic ophthalmic disorders. 5. Diabetic retinopathy and the effect of photocoagulation," *Am J Ophthalm,* 76(2):279–83 (Aug. 1973).

Miyamoto, K. et al., "Prevention of leukostasis and vascular leakage in streptozotocin–induced diabetic retinopathy via intercellular adhesion molecule–1 inhibition," *PNAS Vol.* 96(19):10836–10841 (Sep. 1999).

Barouch, F. C. et al., "Integrin–mediated neutrophil adhesion and retinal leukostasis in diabetes," *Investig Ophthalm Visual Sc,* 41(5):1153–8 (Apr. 2000).

Ambati, J., et al., *IOVS,* 41(5):1181–1191 (2000).

Roberts, W.G., et al., "Increased microvascular permeability and endothelial fenestration induced by vascular endothelial growth factor", *J. Cell Sci,* 108:2369–2379 (1995).

Roberts, W.G., et al., "Neovasculature induced by vascular endothelial growth factor is fenestrated", *Cancer Res,* 57:765–772 (1997).

Luscinskas, F.W., et al., "Integrins and dynamic regulators of vascular function", *FASEB J.,* 8:929–938 (1994).

Rosales, C., et al., "Signal transduction by cell adhesion receptors in leukocytes", *Leukocyte Biol,* 57:189–198 (1995).

Braun, R.D., et al., "Decreased deformability of polymorphonuclear leukocytes in diabetic cats", *Microcirculation,* 3:271–278 (1996).

Shen, H., et al., "Characterization of vascular permeability factor/vascular endothelial growth factor receptors on mononuclear phagocytes", *Blood,* 81:2767–2773 (1993).

Nathan, D.M., "The pathophysiology of diabetic complications: how much does the glucose hypothesis explain?," *Annual Intern Med,* 123(1 Pt 2): 86–89 (1996).

Porta, M., "Diabetic retinopathy and metabolic control," *European Journal of Ophthalmolgy* 3(4): 207–215 (1993).

Lightman, S. "Does aldose reductase have a role in the development of the ocular complications of diabetes?," *Eye* 7(Pt. 2): 238–241 (1993).

Frank, R.N., "On the pathogenesis of diabetic retinopathy. A 1990 update" *Ophthalmology* 98(5): 586–593 (1991).

Wiedemann, P., "What is th etiology of diabetic retinopathy?" *Ophthalmologe* 90(5): 426–433 (1993).

Kessler, L,et al., "Von Willebrand factor in diabetic angiopathy" *Diabetes Metabolism* 24(4): 327–336 (1998). English Abstract and reference in German.

Ways, D.K., and Sheetz, M.J., *Vitamin Hormone* 60: 149–193 (2000).

Antonetti, D.A., et al., "Molecular mechanisms of vascular permeability in diabetic retinopathy" *Seminar of Ophthalmology* 14(4): 240–248 (1999).

Diamond, D.S., et al., "A subpopulation of Mac–1 (CD11b/CD18) molecules mediates neutrophil adhesion to ICAM–1 and fibrinogen", *J Cell Biol,* 120:545–556 (1993).

Davenpeck, K.L., et al., "Rat neutrophils express alpha4 and beta1 integrins and bind to vascular cell adhesion molecule–1 (VCAM–1) and mucosal addressin cell adhesion molecule–1 (MadCAM–1)", *Blood,* 91:2341–2346 (1998).

Morohoshi, M., et al., "Glucose–dependent interleukin 6 and tumor necrosis factor production by human peripheral blood monocytes in vitro", *Diabetes,* 45:954–959 (1996).

Kim, J.A., et al., "Evidence that glucose increases monocyte binding to human aortic endothelial cells", *Diabetes,* 43:1103–1107 (1994).

Manduteanu, I., et al., "High glucose induces enhanced moncyte adhesion to valvular endothelial cells via a mechanism involving ICAM–1, VCAM–1 and CD18", *Endothelium,* 6:315–324 (1999).

Springer, T.A., "Adhesion receptors of the immune system," *Nature (London),* 346:425–434 (1990).

Luscinskas, F.W., et al., "Cytokine–Activated Human Endothelial Monolayers Support Enhanced Neutrophil Transmigration via a Mechanism Involving Both Endothelial–Leukocyte Adhesion Molecule–1 and Intercellular Adhesion Molecule–1," *J. Immunol.,* 146:1617–1625 (1991).

Del Maschio, A., et al., "Polymorphonuclear Leukocyte Adhesion Triggers the Disorganization of Endothelial Cell–to–Cell Adherens Junction," *J. Cell Biol.,* 135:497–510 (1996).

Bolton, S.J., et al., "Loss of the Tight Junction Proteins Occludin and Zonula Occludens–1 from Cerebral Vascular Endothelium During Neutrophil–Induced Blood–Brain Barrier Breakdown In Vivo," *Neuroscience,* 86:1245–1257 (1998).

Kurose, I., et al., "Molecular Determinants of Reperfusion–Induced Leukocyte Adhesion and Vascular Protein Leakage," *Circ. Res.,* 74:336–343 (1994).

Vinores, S.A., et al., "Rapid Communication," *Am. J. Pathol.,* 134:231–235 (1989).

Yamana, Y., et al., "Reflow of obstructed capillaries in the maculae of humans with diabetic retinopathy, observed by fluorescein angiography," *Br. J. Ophthalmol.,* 72:660–665 (1988).

Bandello, F., et al., "Spontaneous Regression of Neovascularization at the Disk and Elsewhere in Diabetic Retinopathy," *Am. J. Ophthalmol.,* 122:494–501 (1996).

Takahaashi, K., et al., "Reperfusion of Occluded Capillary Beds in Diabetic Retinopathy," *Am. J. Ophthalmol.,* 126:791–797 (1998).

Wierusz–Wysocka, B., et al., "Evidence of Polymorphonuclear Neutrophils (PMN) Activation in Patients with Insulin–Dependent Diabetes Mellitus," *J. Leukocyte Biol.,* 42:519–523 (1987).

Lutty, G.A., et al., "Relationship of Polymorphonuclear Leukocytes to Capillary Dropout in the Human Diabetic Choroid," *Am. J. Pathol.,* 151:707–714 (1997).

Tolentino, M.J., et al., "Intravitreal injections of vascular endothelial growth factor produce retinal ischemia and microangiopathy in an adult primate", *Ophthalmology,* 103:1820–1828 (1996).

Okamoto, N., et al., "Trangenic mice with increased expression of vascular endothelial growth factor in the retina", *Am. J. Pathol.,* 151:281–291 (1997).

Aiello, L.P., et al., "Vascular endothelial growth factor–induced retinal permeability is mediated by protein kinase C in vivo and suppressed by an orally effective beta–isoform-selector–inhibitor", *Diabetes,* 46:1473–1480 (1997).

Adamis, A.P., et al., "Increased vascular endothelial growth factor levels in the vitreous of eyes with proliferative diabetic retinopathy", *Am. J. Ophthalmol.,* 118:445–450 (1994).

Aeillo, L.P., et al., "Vascular endothelial growth factor in ocular fluid of patients with diabetic retinopathy and other retinal disorders", *N Eng J Med,* 331:1480–1487 (1994).

Malecaze, F., et al., "Detection of vascular endothelial growth factor messanger RNA and vascular endothelial growth factor–like activity in proliferative diabetic retinopathy", *Arch. Ophthalmol.,* 112:1476–1482 (1994).

Melder, R.J., et al., "During angiogenesis, vascular endothelial growth factor and basic fibroblast growth factor regulate natural killer cell adhesion to tumor endothelium", *Nature Med,* 2:992–997 (1996).

Becker, M.D., et al., "In vivo significance of ICAM–1–dependent leukocyte adhesion in early corneal angiogenesis", *Invest. Ophthalmol. Vis. Sci.,* 40:612–618 (1999).

Detmar, M., et al., *J Invest Dermatol,* 111:1–6 (1998).

Yaccino, J.A., et al., *Curr Eye Res,* 16:761–768 (1997).

Esser, S., et al., *J. Cell Biol,* 140:947–959 (1998).

\* cited by examiner

PREVENTION AND TREATMENT FOR RETINAL ISCHEMIA AND EDEMA

RELATED APPLICATION

This application claims the benefit of U.S. Provisional Application No. 60/114,221, filed Dec. 30, 1998, the entire teachings of which are incorporated herein by reference.

BACKGROUND OF THE INVENTION

Diabetes effects over 16 million Americans. The World Health Organization indicates that diabetes afflicts 120 million people worldwide, and estimates that this number will increase to 300 million by the year 2025. Diabetics are faced with numerous complications including kidney failure, non-traumatic amputations, an increase in the incidence of heart attack or stroke, nerve damage, and loss of vision. Diabetic retinopathy is a form of visual impairment suffered by diabetics.

In particular, diabetic retinopathy is responsible for 13.1% and 18.2% newly reported cases of blindness for men and women, respectively. Kohner E. M., et al. *Diabetic Retinopathy Metabolism*, 25:1985–1102 (1975). The prevalence of blind diabetics in the population is about 100 people per million. Id.

Less than optimal methods of treatment for diabetic retinopathy exist. For example, laser treatment may be used to slow the progression of edema, but cannot be used to reverse it. Accordingly, a need exists to develop effective methods of treatment to reduce or impede vision loss and/or diabetic retinopathy.

SUMMARY OF THE INVENTION

The present invention relates to methods for inhibiting the binding of a leukocyte to an endothelial cell or another leukocyte, more specifically, in the retinal vasculature and/or capillaries. The present invention pertains to methods of treating (e.g., reducing or preventing) retinal injury in a mammal (e.g., patient) wherein the injury involves retinal edema or retinal ischemia, comprising administering a compound that inhibits the binding of a leukocyte to endothelium or to another leukocyte wherein a reduction in edema (e.g., vascular leakage) or ischemia (e.g., non-perfusion) occurs. The compound comprises an integrin antagonist (e.g., lymphocyte function associated molecule-1 (LFA-1), MAC-1 or p150,95), a selectin (e.g., P-selectin, E-selectin and L-selectin) antagonist, an adhesion molecule antagonist (e.g., Intercellular Adhesion Molecule (ICAM)-1, ICAM-2, ICAM-3 or Vascular Cell Adhesion Molecule (VCAM)), or a leukocyte adhesion inducing cytokine antagonist (e.g., Tumor Neucrosis Factor-α (TNF-α) and Interleukin-1β (IL-1β)). The antagonist can be administered with or without a carrier (e.g., pharmaceutically acceptable carrier).

In particular, the invention pertains to methods of treating or preventing retinal injury in a patient comprising administering an intercellular adhesion molecule antagonist. The antagonist can be administered in a carrier (e.g., a pharmaceutically acceptable carrier). The antagonist for intercellular adhesion molecule can be a VCAM, ICAM-2 or ICAM-3 antagonist or, preferably, an ICAM-1 antagonist. In particular, the antagonist can be an antibody or an antibody fragment which is specific for ICAM-1, or an antisense molecule that hybridizes to the nucleic acid sequence which encodes ICAM-1.

The invention also pertains to a method of treating a patient having retinopathy or at risk for retinopathy (e.g., diabetic retinopathy) comprising administering an antagonist (e.g., ICAM-1, ICAM-2 or ICAM-3), as described herein. The antagonist can optionally be administered in a suitable carrier (e.g., pharmnaceutically acceptable carrier). Administration of this antagonist results in a decrease in retinal ischemia and/or retinal edema. Preferably, a decrease in ischemia occurs by at least about 10%, and more preferably, by about 20%, 30%, 40%, 50%, 60%, 70%, 80%, or 90% (e.g., between 10% and 90%). A decrease in edema can occur by at least about 50%, 60%, 70%, 80%, 90% or preferably, by about 95% (e.g., between 50% and 95%). Accordingly, the claimed invention also relates to methods for treating or preventing retinal edema and/or retinal ischemia comprising administering an ICAM antagonist (e.g., ICAM-1), wherein a decrease in the edema and/or ischemia occurs.

The present invention also relates to methods of treating diabetic retinopathy by comprising administering an ICAM-1 antagonist and at least one additional antagonist that inhibits the binding of a leukocyte to an endothelial cell or to another leukocyte. The additional antagonist can be an integrin antagonist, a selectin antagonist, a leukocyte adhesion inducing antagonist, or another adhesion molecule antagonist. The additional antagonist can be another ICAM antagonist (e.g., an antagonist that is specific for a different portion or epitope of the ICAM-1 molecule) or a VCAM antagonist. The types of integrin antagonists, selectin antagonists, and leukocyte adhesion inducing antagonists are described herein.

The invention also encompasses a method of inhibiting leukocyte interaction, comprising contacting a leukocyte, an endothelial cell or a leukocyte adhesion inducing cytokine, with a compound or antagonist, as defined herein. The compound can be an integrin antagonist, a selectin antagonist, an adhesion molecule antagonist or a leukocyte adhesion inducing cytokine antagonist. In particular, the invention relates to a method of inhibiting leukocyte interaction, comprising contacting an endothelial cell with an adhesion molecule antagonist (e.g., ICAM-1 specific antagonist).

Advantages of the present invention include effective treatment for retinopathy, retinal edema, retinal ischemia and other associated disease. Treatment of these diseases and/or conditions have been ineffective until the discovery of the present invention. For the first time, the present invention provides useful methods of treatment which target molecules that are involved in these diseases.

BRIEF DESCRIPTION OF THE FIGURES

FIG. 2A and FIG. 2B show the retinal area after seven days of diabetes. FIG. 2C and FIG. 2D show the retinal area after eight days of diabetes. FIG. 2A and FIG. 2C are photographs from orange leukocyte fluorography (AOLF) and FIG. 2B and FIG. 2D are photographs from fluorescein angiography.

FIGS. 3A and 3B show the retinal area after one week, FIGS. 3C and 3D show the retinal area after two weeks, and FIGS. 3E and 3F show the retinal area after four weeks. FIGS. 3A, 3C, and 3E are photographs from AOLF and FIGS. 3B, 3D and 3F are photographs from fluorescein angiography.

DETAILED DESCRIPTION OF THE INVENTION

The invention relates to methods of treating and/or preventing retinal injury in a mammal by administering a compound that inhibits the binding of a leukocyte to an endothelial cell (e.g., intercellular adhesion molecule-1 antagonist). The retinal injury can be the result of retinopathy or a visually related disease that involves leukocyte occlusion in blood vessels (e.g., capillaries). In particular, the claimed methods pertain to treating diabetic retinopathy.

Diabetic retinopathy is a progressive degeneration of retinal blood vessels and is a consequence of diabetes, in particular, diabetes mellitus. One important aspect of the disease is retinal edema. Fluid build up from deteriorating blood vessels and capillaries causes edema. As the disease progresses, the damage proliferates and large hemorrhages and retinal detachment can result. Retinopathy also refers to noninflammatory degenerative diseases of the retina. The methods of the present invention encompass retinopathy or a visually-related disease that is characterized by one or more of the following retinal signs: capillary obstruction, nonperfusion, formation of vascular lesions and/or proliferation of new blood vessels in association with ischemic areas of the retina. Other disorders or diseases implicated by the invention involve diseases which result in retinal edema and/or retinal ischemia. Examples of such disease include vein occlusions, sickle cell retinopathy, radiation retinopathy, and retinopathy prematurity.

Capillary occlusions constitute a characteristic pathologic feature in early diabetic retinopathy, and are presumed to initiate neovascularization. Microaneurysms, intraretinal microvascular abnormalities and vasodilation are commonly found in early stages of diabetic retinopathy and have been correlated to capillary occlusions. Schroder, S. et al., *American Journal of Pathology*, 139 (81), 81–100 (1991). Leukocytes cause capillary obstruction that is involved in diabetic retinopathy. This obstruction is the result of the leukocytes' large cells volume and high cytoplasmic rigidity. Leukocytes can become trapped in capillaries under conditions of reduced perfusion pressure (e.g., caused by vasoconstriction) or in the presence of elevated adhesive stress between leukocytes and the endothelium, endothelial swelling, or narrowing of the capillary lumen by perivascular edema. Id. Examples of leukocytes include granulocytes, lymphocytes, monocytes, neutrophils, eosinophils, and basophils. Elevated adhesive stress can result from release of chemotactic factors or expression of adhesion molecules on leukocytes or endothelial cells.

A number of glycoproteins exists that are involved in the adhesion of leukocytes. In the case of neutrophils and monocytes, a family of glycoproteins, known as integrins, have been identified. This family of integrins include Lymphocyte Function Associated Antigen-1 (LFA-1), Mac-1, and p150,95. A corresponding family of glycoproteins, referred to as selectins, are expressed in endothelial cells or can be induced by stimulation with endotoxins or cytokines. The selectins include P-selectin, E-selectin, and L-selectin.

The selectin family is involved endothelial interaction. Firm adhesion of activated polymorphonuclear neutrophils (PMN) to the endothelial cells occur through the interaction between integrins (e.g., LFA-1, MAC-1 and P150,95) expressed on the PMNs and members of the immunoglobulin superfamily of proteins, referred to as Intercellular Adhesion Molecule-1 (ICAM-1) and Vascular Cell Adhesion Molecule (VCAM), expressed by the endothelium. Additionally, cytokines such as Tumor Neucrosis Factor-$\alpha$ (TNF-$\alpha$) and Interleukin-1$\beta$ (IL-1$\beta$) can induce the surface expression of ICAM-1, VCAM-1, and E-selectin on endothelial cells. McLeod, D. S. et al., *American Journal of Pathology*, 147:3, p. 642–653, 643 (1995).

Intercellular adhesion molecules are involved in and are important for inflammation responses. Mediators of inflammation cause an induction of ICAM-1 expression on various cell types and sites of inflammation. Both soluble and membrane forms of ICAM-1 exist. Roep, B. O. et al., *Lancet* 343, 1590–1593, 1590 (1994). ICAM-1 is an inducible cell surface ligand for LFA-1. Larson, R. S., et al., *Immunological Reviews*, 114, 181–217, 192(1990). ICAM-1 is a single chain glycoprotein with a peptide backbone of 55 kD. ICAM-1 is a member of immunoglobulin super family consisting of 5 immunoglobulin-like domains. ICAM-1 is expressed or induced by inflammatory mediators on many cell types including endothelial cells, epithelial cells, keratinocytes, synovial cells, lymphocytes, and monocytes. The LFA-1 binding site is the first immunoglobulin domain of ICAM-1. ICAM-1 can also bind with Mac-1. Various forms of ICAM-1 can be used to generate antagonists, such as antibodies or antisense molecules.

The terms, "protein," "polypeptide," or "antibody," include proteins and polypeptides that are integrins (LFA-1, Mac-1 or p150,95) antagonists, adhesion molecules (e.g., ICAM-1 or VCAM) antagonists, selectin antagonists (e.g., P-selectin, L-selectin or E-selectin), or leukocyte adhesion inducing antagonists (e.g. TNF-$\alpha$ or IL-1$\beta$). These terms also include proteins and polypeptides that have amino acid sequences analogous to the amino acid sequence of the protein, as described herein, and/or functional equivalents thereof. These terms also encompass various analogues, homologues, or derivatives thereof. Analogous amino acid sequences are defined to mean amino acid sequences with sufficient identity to the antagonist's amino acid sequence so as to possess its biological activity. For example, an analogous peptide can be produced with "silent" changes in amino acid sequence wherein one, or more, amino acid residues differ from the amino acid residues of the protein, yet still possess its biological activity. Examples of such differences include additions, deletions, or substitutions of residues of the amino acid sequence of the protein or polypeptide. Also encompassed by these terms, are analogous polypeptides that exhibit greater, or lesser, biological activity of the antagonist.

The term "protein" and "nucleic acid sequence" include homologues, as defined herein. The homologous proteins and nucleic acid sequences can be determined using methods known to those of skill in the art. Initial homology searches can be performed at NCBI against the GenBank (release 87.0), EMBL (release 39.0), and SwissProt (release 30.0) databases using the BLAST network service. Altshul, SF, et al,*J. Mol. Biol*. 215: 403 (1990); Altschul, SF., *Nucleic Acids Res*. 25:3389–3402 (1998). the teachings of both are incorporated herein by reference. Computer analysis of nucleotide sequences can be performed using the MOTIFS and the FindPatterns subroutines of the Genetics Computing Group (GCG, version 8.0) software. Protein and/or nucleotide comparisons can also be performed according to Higgins and Sharp (Higgins, D. G. and P. M. Sharp, "Description of the method used in CLUSTAL," *Gene*, 73: 237–244 (1988)). Homologous proteins arid/or nucleic acid sequences are defined as those molecules with greater than 70% sequences identity and/or similarity (e.g., 75%, 80%, 85%, 90%, or 95% homology).

Biologically active derivatives or analogs of the proteins described herein also include peptide mimetics. Peptide mimetics can be designed and produced by techniques known to those of skill in the art. (see e.g., U.S. Pat. Nos. 4,612,132; 5,643,873 and 5,654,276, the teachings of which are incorporated herein by reference). These mimetics can be based, for example, on the protein's specific amino acid sequence and maintain the relative position in space of the corresponding amino acid sequence. These peptide mimetics possess biological activity similar to the biological activity of the corresponding peptide compound, but possess a "biological advantage" over the corresponding amino acid sequence with respect to one, or more, of the following properties: solubility, stability and susceptibility to hydrolysis and proteolysis.

Methods for preparing peptide mimetics include modifying the N-terminal amino group, the C-terminal carboxyl group, and/or changing one or more of the amino linkages in the peptide to a non-amino linkage. Two or more such modifications can be coupled in one peptide mimetic molecule. Modifications of peptides to produce peptide mimetics are described in U.S. Pat. Nos. 5,643,873 and 5,654,276, the teachings of which are incorporated herein by reference. Other forms of the proteins, polypeptides and antibodies described herein and encompassed by the claimed invention, include those which are "functionally equivalent." This term, as used herein, refers to any nucleic acid sequence and its encoded amino acid which mimics the biological activity of the protein, polypeptide or antibody and/or functional domains thereof.

The present methods utilize various forms of antagonists. An antagonist, as defined herein, means a compound that can inhibit, either partially or fully, the binding of a leukocyte to an endothelial cell or to another leukocyte. An antagonist's biological activity also refers to a compound that can reduce or lessen the interaction between a leukocyte and an endothelial cell, or another leukocyte. Such antagonists include integrin antagonists (e.g., an antagonist for the LFA-1, Mac-1, and p150,95 integrin glycoproteins), selectin antagonists (e.g., antagonists for P-selectin, E-selectin and L-selectin) and adhesion molecule antagonists (e.g., ICAM-1, ICAM-2, ICAM-3 antagonist or VCAM antagonist) or a leukocyte adhesion inducing cytokine antagonist (an antagonist for TNF-α and IL-1β). These antagonists include antibody or antibody fragments, peptide mimetics molecules, antisense molecules, ribozymes, aptamers (nucleic acid molecules), and small molecule antagonists. Soluble ICAM can also act as an antagonist because it can bind to the leukocyte, thereby preventing the membrane bound ICAM from binding.

Several ICAM-1 antagonists exist. An ICAM-1 antagonist is a composition capable of inhibiting the binding of ICAM-1 to a receptor or has the ability to decrease or affect the function of ICAM-1. Such antagonists include antibodies to ICAM-1 (e.g., the IA29 antibody), antisense molecules that hybridize to nucleic acid which encodes ICAM-1. ICAM-1 antagonists also include ribozymes, aptimers, or small molecule inhibitors that are specific for ICAM-1 or the nucleic acid that encodes ICAM-1. Antagonists of ICAM-1 include compounds which inhibit the binding between LFA-1 or Mac-1 and ICAM-1, or compounds that reduce the biological activity or function of ICAM-1. The biological activity of ICAM-1 refers to the ability to bind to LFA-1 and/or Mac-1, and/or the ability to induce leukocyte adhesion.

The terms "antibody" or "immunoglobulin" refer to an immunoglobulin or fragment thereof having specificity to a molecule involved in leukocyte-leukocyte interaction or leukocyte-endothelium interaction. Examples of such antibodies include anti-integrin antibodies (e.g., antibodies specific to LFA-1, Mac-1 or p150,35), anti-selectin antibodies (e.g., antibodies specific to P-selection, E-selection and L-selectin), antibodies to leukocyte adhesion inducing cytokines (e.g., TNF-1α and IL-1β antibodies) and adhesion molecule antibodies (e.g., ICAM-1, ICAM-2, ICAM-3 or VCAM antibodies).

The terms "ICAM-1 antibody," or "ICAM-1 immunoglobulin" refer to immunoglobulin or fragment thereof having specificity for ICAM-1. The term, "antibody" is intended to encompass both polyclonal and monoclonal antibodies including transgenically produced antibodies. The terms polyclonal and monoclonal refer to the degree of homogeneity or an antibody preparation and are not intended to be limited to particular methods of production. An antibody (e.g., anti-ICAM-1 antibody) can be raised against an appropriate immunogen, such as an isolated and/or recombinant polypeptide (e.g., ICAM-1) or portion thereof (including synthetic molecules such as synthetic peptides). In one embodiment, antibodies can be raised against an isolated and/or recombinant antigen or portion thereof (e.g., a peptide) or against a host cell which expresses recombinant antigen or a portion thereof. In addition, cells expressing recombinant antigen (e.g., ICAM-1), such as transfected cells, can be used as immunogens or in a screening for an antibody which binds the receptor.

Preparation of immunizing antigen, and polyclonal and monoclonal antibody production, can be performed using any suitable technique. A variety of methods have been described (see e.g., Kohler et al., *Nature*, 256:495–497 (1975) and *Eur. J. Immunol*. 6: 511–519 (1976); Milstein et al.,*Nature* 266:550–552 (1977); Koprowski et al., U.S. Pat. No. 4,172,124; Harlow, E. and D. Lane, 1988, *Antibodies: A Laboratory Manual*, (Cold Spring Harbor Laboratory: Cold Spring Harbor, N.Y.); *Current Protocols In Molecular Biology*, Vol. 2 (Supplement 27, Summer' 94), Ausubel, F.

M. et al., Eds., (John Wiley & Sons: New York, N.Y.), Chapter 11, (1991)).

Following immunization, anti-peptide antisera can be obtained from the immunized animal, and if desired, polyclonal antibodies can be isolated from the serum. As described herein, purified recombinant proteins generated in E. coli were used to immunize rabbits to generate specific antibodies directed against the antigen. These antibodies recognize the recombinant protein expressed in E. coli. Monoclonal antibodies can also be produced by standard techniques which are well known in the art (Kohler and Milstein, Nature 256:495–497 (1975); Kozbar et al., Immunology Today 4:72 (1983); and Cole et al., Monoclonal Antibodies and Cancer Therapy, Alan R. Liss, Inc., pp. 77–96 (1985)). Generally, a hybridoma is produced by fusing a suitable immortal cell line (e.g., a myeloma cell line such as SP2/0) with antibody producing cells. The antibody producing cell, preferably those of the spleen or lymph nodes, can be obtained from animals immunized with the antigen of interest. The fused cells (hybridomas) can be isolated using selective culture conditions, and cloned by limiting dilution. Cells which produce antibodies with the desired specificity can be selected by a suitable assay (e.g., ELISA).

Other suitable methods of producing or isolating antibodies of the requisite specificity can be used, including, for example, methods which select recombinant antibody from a library, by PCR, or which rely upon immunization of transgenic animals (e.g., mice) capable of producing a full repertoire of human antibodies (see e.g., Jakobovits et al., Proc. NatL Acad. Sci. USA, 90: 2551–2555 (1993); Jakobovits et al., Nature, 362: 255–258 (1993); Lonberg et al., U.S. Pat. No. 5,545,806; Surani et al., U.S. Pat. No. 5,545,807).

For example, the monoclonal antibody, IA29 can be used as described herein. The IA29 antibody is specific for ICAM-1, and can be purchased from R and D Systems, Minneapolis, Minn.

Functional fragments of antibodies, including fragments of chimeric, humanized, primatized, veneered or single chain antibodies, can also be produced. Functional fragments or portions of the foregoing antibodies include those which are reactive with the antigen (e.g., ICAM-1). For example, antibody fragments capable of binding to the antigen (e.g., ICAM-1) or portion thereof, including, but not limited to, Fv, Fab, Fab' and F(ab')$_2$ fragments are encompassed by the invention. Such fragments can be produced by enzymatic cleavage or by recombinant techniques. For instance, papain or pepsin cleavage can generate Fab or F(ab')$_2$ fragments, respectively. Antibodies can also be produced in a variety of truncated forms using antibody genes in which one or more stop codons has been introduced upstream of the natural stop site. For example, a chimeric gene encoding a F(ab')$_2$ heavy chain portion can be designed to include DNA sequences encoding the $CH_1$ domain and hinge region of the heavy chain.

It will be appreciated that the antibody can be modified, for example, by incorporation of or attachment (directly or indirectly (e.g., via a linker)) of a detectable label such as a radioisotope, spin label, antigen (e.g., epitope label such as a FLAG tag) or enzyme label, flourescent or chemiluminescent group and the like, and such modified forms are included within the term "antibody."

A suitable antagonist is also an antisense molecule that can hybridize to the nucleic acid which encodes the antagonist (e.g., ICAM-1). The hybridization inhibits transcription and synthesis of the protein. Antisense molecules or constructs can be made using method known in the art. DeMesmaeker, Alain, et al., Acc Chem. Res. 28:366–374 (1995), Setlow, Jane K., Genetic Engineering, 20:143–151 (1998); Dietz, Pat. No. 5,814,500, filed Oct. 31, 1996, entitled, "Delivery Construct for Antisense Nucleic Acids and Method of Use," the teachings all of which are incorporated by reference in their entirety. In particular, constructing an antisense molecule for an ICAM-1 antagonist is described in detail in WO 97/46671, entitled, "Enhanced Efficacy of Liposomal Anti-sense Delivery," the teachings of which are incorporated by reference in their entirety. Additionally, developing an antisense molecule to inhibit a retinal disorder (e.g., retinopathy) is described in Robinson, G. S., et al., Proc. Natl. Acad. Sci. 93:4851–4856 (1996).

The invention relates to treating retinal injury wherein the retinal injury involves retinal edema and/or retinal ischemia, comprising administering a compound that inhibits the binding of a leukocyte to an endothelial cell or another leukocyte in, for example, a blood vessel or capillary, which results in the reduction of retinal edema and/or retinal ischemia. The term retinal injury is defined herein as a decreased ability for the retina to function normally as measured, for example, by the patient's vision, electrical signal or potential, or fluorescein angiograms. The compound has the ability to inhibit or reduce leukocyte occlusion in the retinal vascular. As described herein, the compound can be an integrin antagonist, a selectin antagonist, a leukocyte adhesion inducing cytokine antagonist, or, preferably, an adhesion molecule antagonist (e.g., an ICAM-1, ICAM-2, or ICAM-3 antagonist). The invention also pertains to administering an ICAM-1 antagonist to treat retinal edema, retinal ischemia, and/or diabetic retinopathy. The various forms of the antagonists are described herein.

The invention includes methods of inhibiting leukocyte interaction, comprising contacting a leukocyte or endothelial cell with an antagonist. For example, using the various antagonists described herein, one can contact a leukocyte with an integrin antagonist, an endothelial cell with an adhesion molecule antagonist or a selectin antagonist, or subject the cytokines that induce surface expression of ICAM-1, VCAM-1, and E-selectin to a leukocyte adhesion inducing cytokine antagonist.

The invention further comprises the use of an ICAM-1 antagonist in conjunction with a second antagonist. Genetic variability that exists among various patient populations and/or additional mechanisms can warrant administering more than one antagonist. For example, the claimed methods include administering an ICAM-1 antagonist, which is specific to a particular epitope of ICAM-1, and an additional ICAM-1 antagonist, which is specific to a different epitope or genetic variation. Similarly, an ICAM-1 antagonist can be administered with any one of the antagonists described herein. Administering a combination of antagonists to prevent the leukocyte adhesion to endothelial cells and/or leukocytes can result in even more effective treatment of diabetic retinopathy or a more dramatic reduction in retinal edema and/or ischemia. The combination of antagonists can be administered at substantially the same time, or sequentially, with suitable intervals between administration of the antagonists.

The invention also relates to decreasing or reducing the amount of ischemia and/or edema present in a patient by administering an effective amount of an ICAM-1 antagonist. Ischemia refers to tissue which lacks proper or suitable blood flow. Ischemia refers to an inadequate circulation of blood flow which can be the result of a mechanical obstruction (e.g., trapped leukocyte) of the blood supply or damage to the blood supplying vessel which results in a reduction of the blood flow. Inadequate blood flow results in reduced tissue oxygenation. Hence, ischemia can be a function of leukostasis, and can be measured by determining the density of trapped leukocytes, as described herein.

Edema refers to the excess leakage that occurs from the capillaries. As described herein, leukocytes become trapped in the capillaries in the conditions of reduced perfusion pressure (e.g., caused by constriction as seen in early stages of diabetes) or in the presence of an elevated adhesive stress between leukocytes and endothelium, endothelial swelling or narrowing of the capillary lumin by perivascular edema. The leukocyte build up causes leakage from the blood vessel. Thus, edema can be measured by determining the amount of retinal vascular albumin permeation, as described herein. The methods of treatment include reducing or decreasing the amount of ischemia and/or edema by administering antagonist that inhibits leukocyte and endothelial cell interaction (e.g., an ICAM-1 antagonist). The decrease in ischemia is at least about 20% and can be greater, such as at least about 30%, 40%, 50% 60%, 70%, 80% or 90%. The decrease in edema is at least about 50%, and can be greater, such as at least about 60%, 70%, 80%, and preferably at least about 90%.

The reduction or decrease of the retinal edema and/or retinal ischemia can be determined as compared to a control, standard, or baseline. The level of edema and/or ischemia can be quantified using methods known in the art, and a decrease, as compared with a control, standard, or baseline, indicates successful treatment. The quantified amounts of edema and/or ischemia can be compared with a suitable control to determine if the levels are decreased. The sample to be tested can be compared with levels for the specific individual from previous time points (e.g., before having diabetic retinopathy, or during various phases of treatment for the diabetic retinopathy), or with levels in normal individuals or suitable controls. An individual who is being treated for diabetic retinopathy can be monitored by determining the levels of edema and/or ischemia at various time points. Such levels of edema and/or ischemia can be determined before treatment, during treatment, and after treatment. A decrease in the level of ischemia and/or edema, as described herein, indicates successful treatment. Ischemia and edema can be measured using methods now known or those developed in the future. See Kohner E. M., et al. *Diabetic Retinopathy Metabolism*, 25:1985–1102 (1975). For example, ischemia and edema can be measured using a fluorescein angiogram or by measuring the vision loss in a patient. Edema (e.g., leakage) can also be assessed by measuring electrical signals or potential, visualizing the retina using a slit lamp or by using a sensitive isotope dilution method.

Administration and Dosages.

The terms "pharmaceutically acceptable carrier" or a "carrier" refer to any generally acceptable excipient or drug delivery device that is relatively inert and non-toxic. The antagonist can be administered with or without a carrier. A preferred embodiment is to administer the antagonist (e.g., ICAM-1 antagonist) to the retinal area or the vasculature around or leading to the retina. Exemplary carriers include calcium carbonate, sucrose, dextrose, mannose, albumin, starch, cellulose, silica gel, polyethylene glycol (PEG), dried skim milk, rice flour, magnesium stearate, and the like. Suitable formulations and additional carriers are described in Remington's Pharmaceutical Sciences, (17th Ed., Mack Pub. Co., Easton, Pa.), the teachings of which are incorporated herein by reference in their entirety. The antagonist can be administered systemically or locally (e.g., by injection or diffusion).

Suitable carriers (e.g., pharmaceutical carriers) also include, but are not limited to sterile water, salt solutions (such as Ringer's solution), alcohols, polyethylene glycols, gelatin, carbohydrates such as lactose, amylose or starch, magnesium stearate, talc, silicic acid, viscous paraffin, fatty acid esters, hydroxymethylcellulose, polyvinyl pyrolidone, etc. Such preparations can be sterilized and, if desired, mixed with auxiliary agents, e.g., lubricants, preservatives, stabilizers, wetting agents, emulsifiers, salts for influencing osmotic pressure, buffers, coloring, and/or aromatic substances and the like which do not deleteriously react with the active compounds. They can also be combined where desired with other active substances, e.g., enzyme inhibitors, to reduce metabolic degradation. A carrier (e.g., a pharmaceutically acceptable carrier) is preferred, but not necessary to administer an antagonist (e.g., an ICAM-1 antagonist).

For parenteral application, particularly suitable are injectable, sterile solutions, preferably oily or aqueous solutions, as well as suspensions, emulsions, or implants, including suppositories. In particular, carriers for parenteral administration include aqueous solutions of dextrose, saline, pure water, ethanol, glycerol, propylene glycol, peanut oil, sesame oil, polyoxyethylene-polyoxypropylene block polymers, and the like. Ampules are convenient unit dosages.

Preferably, the antagonist is administered locally to the eye or retinal area or vasculature (e.g., the posterior limbus or artery). The antagonist can also be administered to the cornea of the eye. The antagonist diffuses into the eye and contacts the retina or surrounding vasculature (e.g., eye drops, creams or gels).

The lipid-modifying (e.g., lipid modulating) compositions of the present invention can be administered intravenously, parenterally, orally, nasally, by inhalation, by implant, by injection, or by suppository. The composition can be administered in a single dose or in more than one dose over a period of time to confer the desired effect.

The actual effective amounts of lipid modifying drug can vary according to the specific drug being utilized, the particular composition formulated, the mode of administration and the age, weight and condition of the patient, for example. As used herein, an effective amount of a lipid-modulating drug is an amount of the drug which is capable of reducing the edema and/or ischemia levels. Dosages for a particular patient can be determined by one of ordinary skill in the art using conventional considerations, (e.g. by means of an appropriate, conventional pharmacological protocol).

EXEMPLIFICATION

This exemplification demonstrates that diabetic retinal vascular leakage and non-perfusion are temporally and spatially associated with retinal leukocyte stasis (leukostasis). The diabetes-induced increase in leukostasis correlates with the increased expression of retinal intercellular adhesion molecule-1 (ICAM-1). Moreover, ICAM-1 blockade with a monoclonal antibody prevents diabetic retinal leukostasis and vascular leakage by 48.5% and 85.6%, respectively. These data identify diabetic retinal eukostasis as an early and important event in the pathogenesis of diabetic retinopathy. hey also indicate the utility of ICAM-1 inhibition as a therapeutic strategy for the revention and treatment of diabetic retinopathy.

The retinal vasculature of humans and rodents with diabetes mellitus contains increased numbers of leukocytes. Many of these leukocytes are static.

Retinal leukostasis was studied with acridine orange leukocyte fluorography (AOLF). Miyamoto, K., et al.,

*Invest. Ophthalmol. Vis. Sci.* 39, 2190 (1998); S. Schroder, S., et al., *Am/J/Pathol.* 139, 81 (1991); Nishiwaki H., et al., *Invest. Ophthalmol. Vis. Sci.* 37, 1341 (1996); K. Miyamoto et al., *Invest. Ophthalmol. Vis. Sci.* 37, 2708 (1996), the teachings of all of these references are incorporated herein by reference in their entirety. Intravenous injection of acridine orange causes leukocytes and endothelial cells to fluoresce through the non-covalent binding of the molecule to double stranded DNA. When a scanning laser ophthalmoscope is utilized, retinal leukocytes and blood vessels can be visualized in vivo. Twenty minutes after acridine orange injection, only static leukocytes are observed due to differential dye washout.

Retinal leukostasis was quantified in Long-Evans rats. All animals experiments followed the Association for Research in Vision and Ophthalmology guidelines. Rats were anesthetized with xylazine hydrochloride (4 mg/kg) (Pheonix Pharmaceutical, St. Joseph, Mo.) and ketamine hydrochloride (25 m/kg) (Parke-Davis, Morris Plains, N.J.). On the day before leukocyte dynamics were observed, each rat had a heparin-lock catheter surgically implanted in the right jugular vein that was subcutaneously externalized to the back of the neck. The left eye was dilated with 1% tropicamide (Alcon, Humancao, Puerto Rico) to observe leukocyte dynamics. The rats were positioned on a movable platform and placed level with the chin rest of the scanning laser ophthalmoscope (SLO) (Rodenstock Instrument, Munich, Germany). A focused image of the peripapillary fundus of the left eye was obtained. Acridine orange (Sigma, St. Louis, Mo.) was dissolved in sterile saline (1.0 mg/ml) and 3 mg/kg was injected through the jugular vein catheter at a rate of 1 ml/min. The fundus was observed with the SLO using the argon blue laser as the illumination source and the standard fluorescein angiography filter in the 40° field setting for 1 minute. Twenty minutes later, the fundus was again observed to evaluate leukostasis in the retina. The images were recorded on a videotape at the rate of 30 frames/sec. The video recordings were analyzed on a computer equipped with a video digitizer (Radius, San Jose, Calif.) that digitizes the video image in real time (30 frames/sec) to 640×480 pixels with an intensity resolution of 256 steps. For evaluating retinal leukostasis, an observation area around the optic disc measuring ten disc diameters in diameter was determined by drawing a polygon surrounded by the adjacent major retinal vessels. The area was measured in pixels and the density of trapped leukocytes was calculated by dividing the number of trapped leukocytes, which were recognized as fluorescent dots, by the area of the observation region. The densities of leukocytes were calculated generally in eight peripapillary observation areas and an average density was obtained by averaging the eight density values. Long-Evans rats weighing approximately 200 g received a single 60 mg/kg injection of streptozotocin (Sigma, St. Louis, Mo.) in 10 mM citrate buffer, pH 4.5, after an overnight fast. Control non-diabetic animals received citrate buffer alone. Animals with blood glucose levels greater than 250 mg/dl 24 hours later were considered diabetic.

Figure 1A:
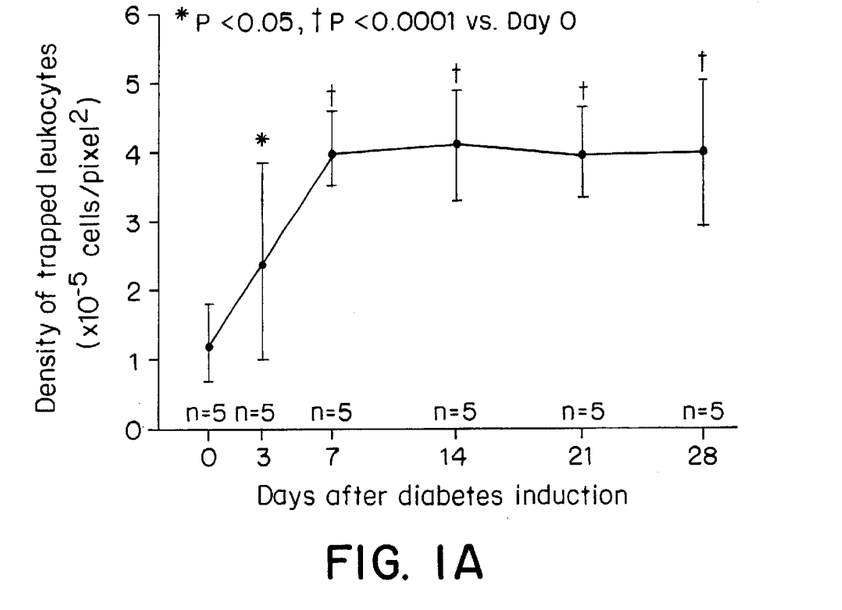
FIG. 1A is a graph showing the density of trapped leukocytes as measured on days after diabetes induction. The graph shows a time course of diabetic retinal leukostasis. All data show the mean±the standard deviation (SD).

Diabetic rats, like humans with diabetes, develop retinal non-perfusion and increased vascular leakage. A time course analysis showed that retinal leukostasis increased 1.9-fold as early as three days following diabetes induction (n=5, p<0.05) (FIG. 1A). Leukostasis was serially quantified using AOLF. Non-diabetic animals (day 0) and animals with streptozotocin-induced diabetes of varying duration were studied. After one week of diabetes, retinal leukostasis was 3.2-fold higher than in non-diabetic controls (n=5, p<0.0001). This finding remained unchanged in degree for three additional weeks (n=5, p<0.0001) (FIG. 1A). Reliable leukostasis quantitation beyond the four week time point was precluded due to cataract formation.

Figure 1B:
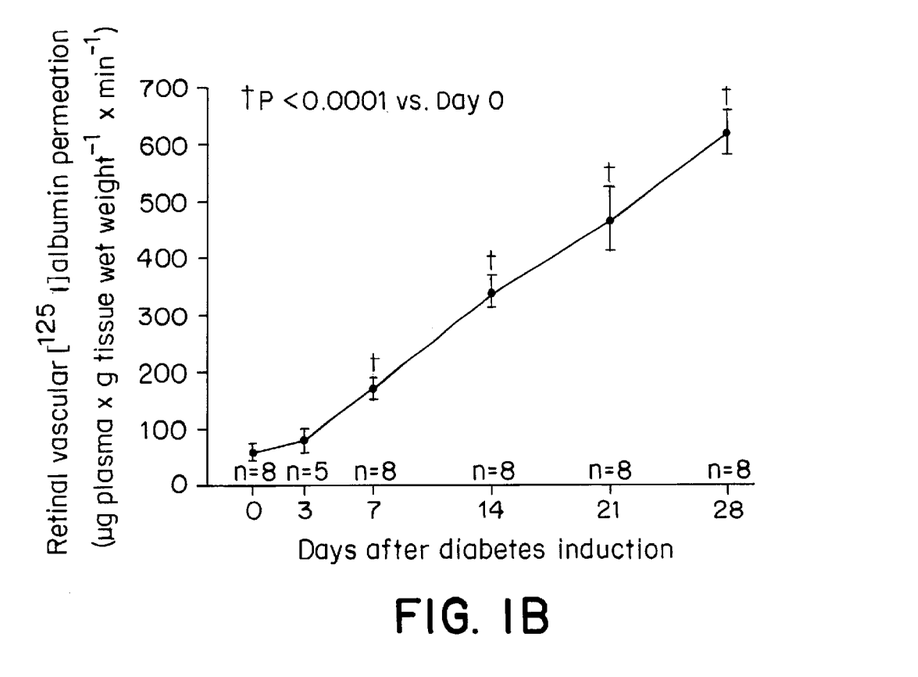
FIG. 1B is a graph showing the retinal vascular [$^{125}$I] albumin permeation as measured against the days after diabetes induction. The graph shows a time course of vascular leakage. All data show the mean±the standard deviation (SD).

The adhesion of leukocytes to endothelial cells can trigger the disorganization of endothelial cell adherens and tight junctions. To determine if the diabetic retinal leukostasis was correlated with blood retinal barrier breakdown and vascular leakage, retinal albumin permeation was quantified (FIG. 1B). Radioactive albumin permeation into retinal tissue was quantitated in separate cohorts of animals at the same time points using the isotope dilution technique. Retinal albumin permeation characterizes human and rodent diabetic retinopathy and can be sensitively quantified using the isotope dilution technique. Tilton, R. G. et al., *Diabetes* 42, 221, (1993); Tilton, R. G. et al., *J. Clin. Invest.* 99, 2192 (1997). Purified monomer BSA (1 mg) was iodinated with 1 mCi of $^{131}$I or $^{125}$I by the iodogen method, as described herein. Polyethylene tubing was used to cannulate the right jugular vein (0.28 mm internal diameter) and the left or right iliac artery (0.58 mm internal diameter). The tubing was filled with heparinized saline (400 U heparin/ml). The right jugular vein cannula was used for tracer injection. The iliac artery cannula was connected to a one ml syringe attached to a Harvard Bioscience model PHD 2000 constant withdrawal pump preset to withdraw at a constant rate of 0.055 ml/min. At time 0, [$^{125}$I]albumin (50 million cpm in 0.3 ml of saline) was injected into the jugular vein and the withdrawal pump started. At the eight minute mark, 0.2 ml (50 million CPM) of [$^{131}$I]BSA was injected. At the ten minute mark, the heart was excised, the withdrawal pump was stopped, and the retina was quickly dissected and sampled for γ-spectrometry. Tissue and arterial samples were weighed and counted in a γ-spectrometer (Beckman 5500, Irvine, Calif.). The data were corrected for background and a quantitative index of [$^{125}$I] tissue clearance was calculated as described herein and expressed as μg plasma×g tissue wet weight$^{-1}$×min$^{-1}$. Briefly, [$^{125}$I] BSA tissue activity was corrected for tracer contained within the tissue vasculature by multiplying [$^{125}$I]BSA activity in the tissue by the ratio of [$^{125}$I]BSA/[$^{131}$I]BSA activities in an arterial plasma sample obtained at the end of the experiment. The vascular-corrected [$^{125}$I]BSA activity was divided by the time-averaged [$^{125}$I]BSA plasma activity (obtained from a well-mixed sample of plasma taken from the withdrawal syringe) and by the tracer circulation time (10 min) and then normalized per gram tissue wet weight.

A time course analysis in diabetic rats revealed a 2.9-fold (n=8, p<0.0001) and 10.7-fold (n=8, p<0.0001) increase in albumin permeation one and four weeks following the induction of diabetes (FIG. 1B). The breakdown of the blood retinal barrier coincided with the maximal observed increases in retinal leukostasis.

Figure 2A:
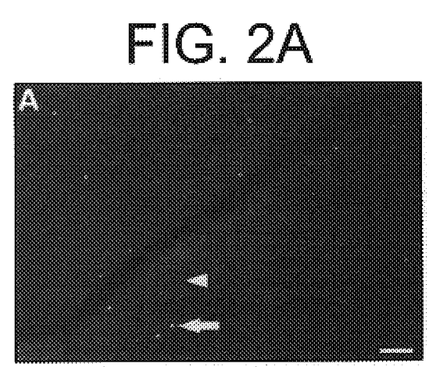
FIGS. 2A–D show four photographs of the same retinal area.
Figure 2B:
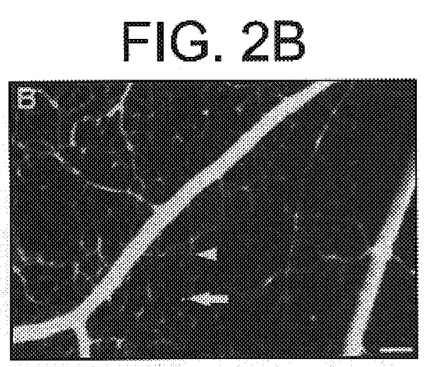
Figure 2C:
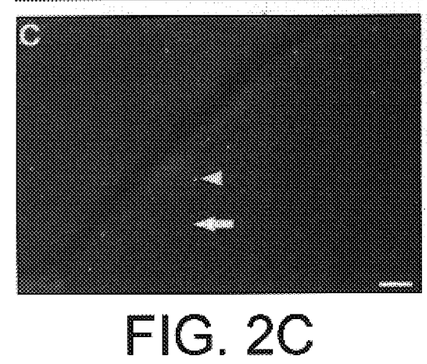
Figure 2D:
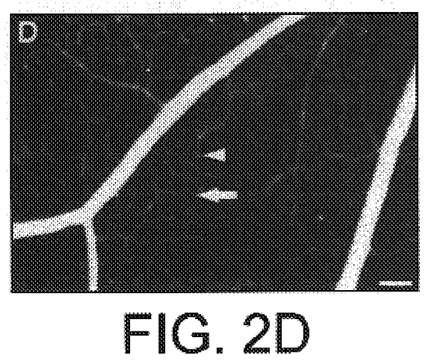

To further characterize the diabetic retinal leukostasis, serial AOLF and fluorescein angiography studies were performed. Immediately after observing and recording the static leukocytes, 20 μl of 1% sodium fluorescein was injected into the jugular vein catheter. FIG. 2 shows that static leukocytes are in flux, block capillary flow and transmigrate. Serial AOLF of static leucocytes in the same retinal area after seven (FIG. 2A) and eight (FIG. 2C) days of diabetes shows their complete replacement within a 24 hour period. The arrow points to a static leukocyte (FIGS. 2A,2B) that appears to have transmigrated (FIG. 2B). One day later, AOLF and fluorescein angiography show that the leukocyte has disappeared (FIGS. 2C,2D). The arrowhead shows a patent (e.g., opened or exposed) capillary (FIG. 2B) that subsequently becomes obstructed by a static leukocyte 24 hours later (FIGS. 2C,2D).

These studies revealed that the individual leukocytes observed with AOLF are in flux, even though the overall degree of leukostasis is constant (FIG. 2). All of the static retinal leukocytes observed seven days following the induction of diabetes are topographically distinct from those seen 24 hours later (FIG. 2). Furthermore, a small proportion of the static leukocytes appears to be in the extravascular space, a result consistent with their rapid transmigration following dye labeling (FIG. 2).

Figure 3A:
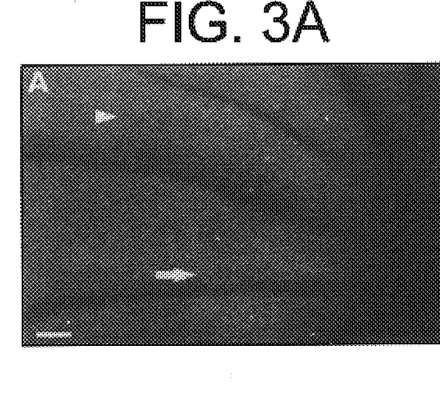
FIGS. 3A–F show six photographs of a retinal area.
Figure 3B:
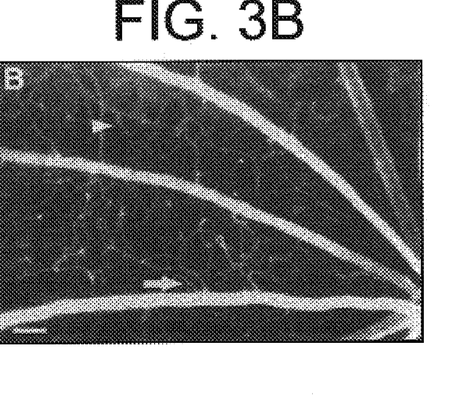
Figure 3C:
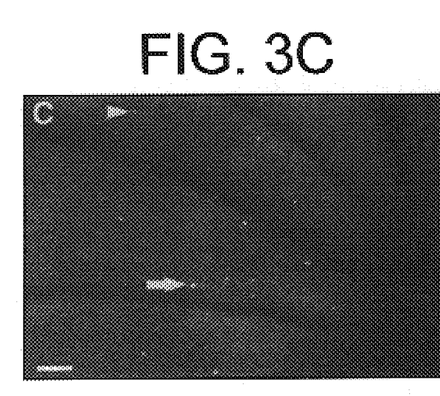
Figure 3D:
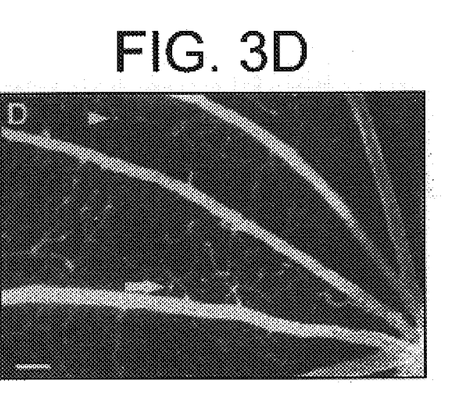
Figure 3E:
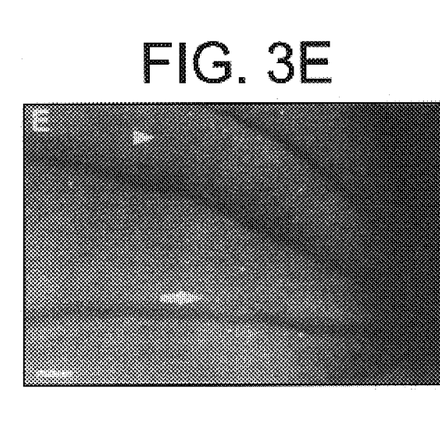
Figure 3F:
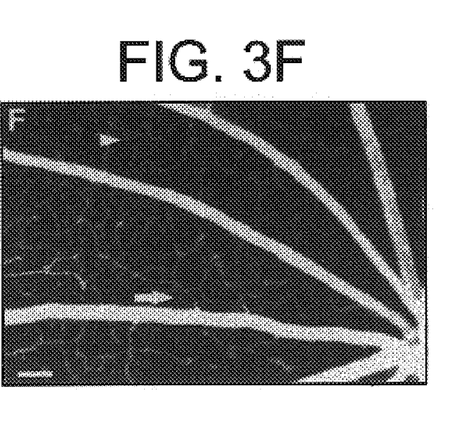

Fluorescein angiography and AOLF were also used to study retinal non-perfusion. FIG. 3 shows leukocyte-induced non-perfusion and reperfusion. Serial studies were completed one (FIGS. 3A,3B), two (FIGS. 3C,3D) and four (FIGS. 3E,3F) weeks following diabetes induction using both AOLF (FIGS. 3A,3C,3E) and fluorescein angiography (FIGS. 3B,3D,3F). The arrow shows a patent capillary (FIG. 3B) that subsequently becomes occluded downstream from a static leukocyte (FIGS. 3C,3D), and then opens up when the leukocyte disappears (FIGS. 3E,3F). The arrowhead shows a patent capillary (FIG. 3B) that becomes occluded downstream from a static leukocyte (FIGS. 3C,3D) and then remains closed after the leukocyte has disappeared (FIGS. 3E,3F).

These studies identified numerous static leukocytes directly associated with areas of downstream non-perfusion (FIGS. 2 and 3). The non-perfused capillaries were patent prior to the onset of the leukostasis, indicating a causal relationship. As the leukocyte(s) disappeared, the capillaries either reperfused or remained closed (FIG. 3). Non-perfusion/reperfusion has been observed in human diabetic retinopathy, but the mechanism remains unexplained. These observations indicate the phenomenon results from transient retinal leukostasis. The cumulative leukostasis may also be operative in the permanent acellular capillary formation and persistent non-perfusion that characterize the later phases of diabetic retinopathy.

ICAM-1 immunoreactivity increases in the retinal vasculature of human eyes with diabetic retinopathy. To determine if retinal ICAM-1 expression increases in association with diabetic retinal leukostasis, ICAM-1 mRNA levels were quantified using the ribonuclease protection assay. The retinas were gently dissected free and cut at the optic disc after enucleation, and frozen immediately in liquid nitrogen. Total RNA was isolated from rat retinas according to the acid guanidinium thiocyanate-phenol-chloroform extraction method. A 425-base pair EcoRI/BamHI fragment of rat ICAM-1 cDNA was prepared by reverse transcription-polymerase chain reaction and cloned into pBluescript II KS vector. A 472 nucleotide antisense riboprobe was prepared by in vitro transcription (Promega, Madison, Wis.) of linearized plasmid DNA with T7 RNA polymerase in the presence of [$^{32}$P]dUTP. The sequence of the cloned cDNA was verified by DNA sequencing. Twenty micrograms of total cellular RNA were used for RNase protection assays. All samples were simultaneously hybridized with an 18S riboprobe (Ambion, Austin, Tex.) to normalize for variations in loading and recovery of RNA. The assays were performed essentially as described herein, (M. Gilman et al., *Current Protocols in Molecular Biology* (John Wiley, N.Y., 1989)) except that organic extraction was replaced with precipitation of the protected fragments from a chaotropic solution (Y. Hod. *Biotechniques* 13,852 (1992)). Protected fragments were separated on a gel of 5% acrylamide, 8M urea, 1×Tris-borate-EDTA, and quantified with a PhosphorImager (Molecular Dynamics, Sunnyvale, Calif.).

FIG. 4 shows that retinal ICAM-1 levels are increased and are required for diabetic retinal leukostasis and blood barrier breakdown. The ribonuclease protection assay demonstrates that retinal ICAM-1 levels are significantly increased seven days following diabetes induction (FIG. 4A). Each lane is the signal from the two retinas of a single animal. The retinal ICAM-1 levels were normalized to 18S RNA (FIG. 4B). Retinas analyzed three days following diabetes induction demonstrate that retinal ICAM-1 mRNA levels were 1.5-fold higher than non-diabetic controls, but this increase was not statistically significant (n=5, p>0.05) (FIGS. 4A and B). However, after one week of diabetes the retinal ICAM-1 levels were 2.2-fold greater and significantly increased when compared to non-diabetic controls (n=4, p<0.05). The ICAM-1 increases temporally coincided with the development of diabetic retinal leukostasis and blood retinal barrier breakdown.

Figure 4A:
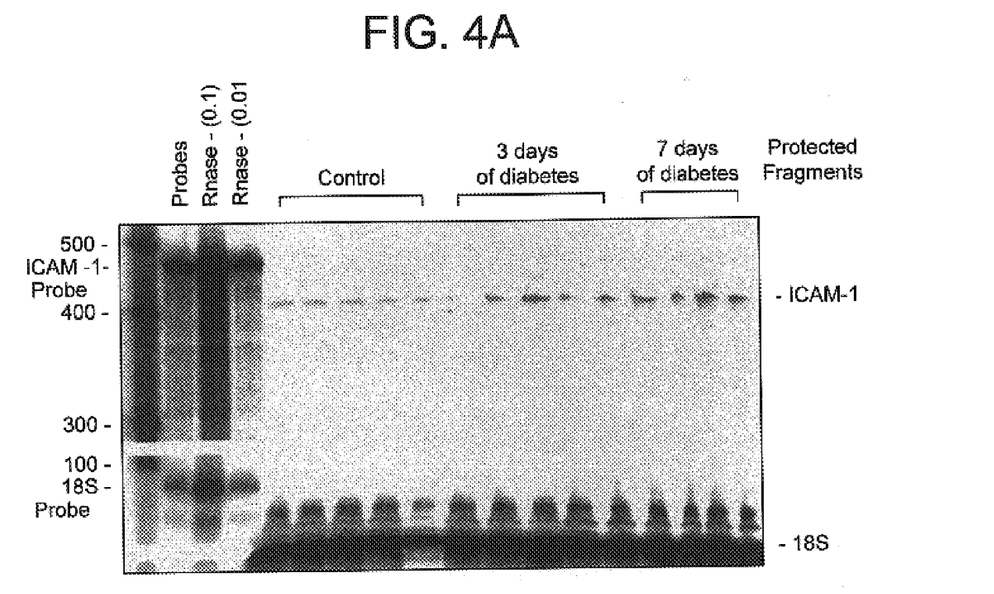
FIG. 4A is a photograph of ribonuclease protection assay results showing ICAM-1 mRNA levels from controls and a diabetic rat three days following diabetes induction. Each lane is the signal from the two retinas of a single animal. The lane labeled "Probes" shows a hundred-fold dilution of the full-length ICAM-1 and 18S riboprobes. The lanes labeled "RNase-(0. 1)" and "RNase-(0.0 1)" show the ten-fold and hundred-fold dilutions, respectively, of the full length riboprobes without sample or RNase.
Figure 4B:
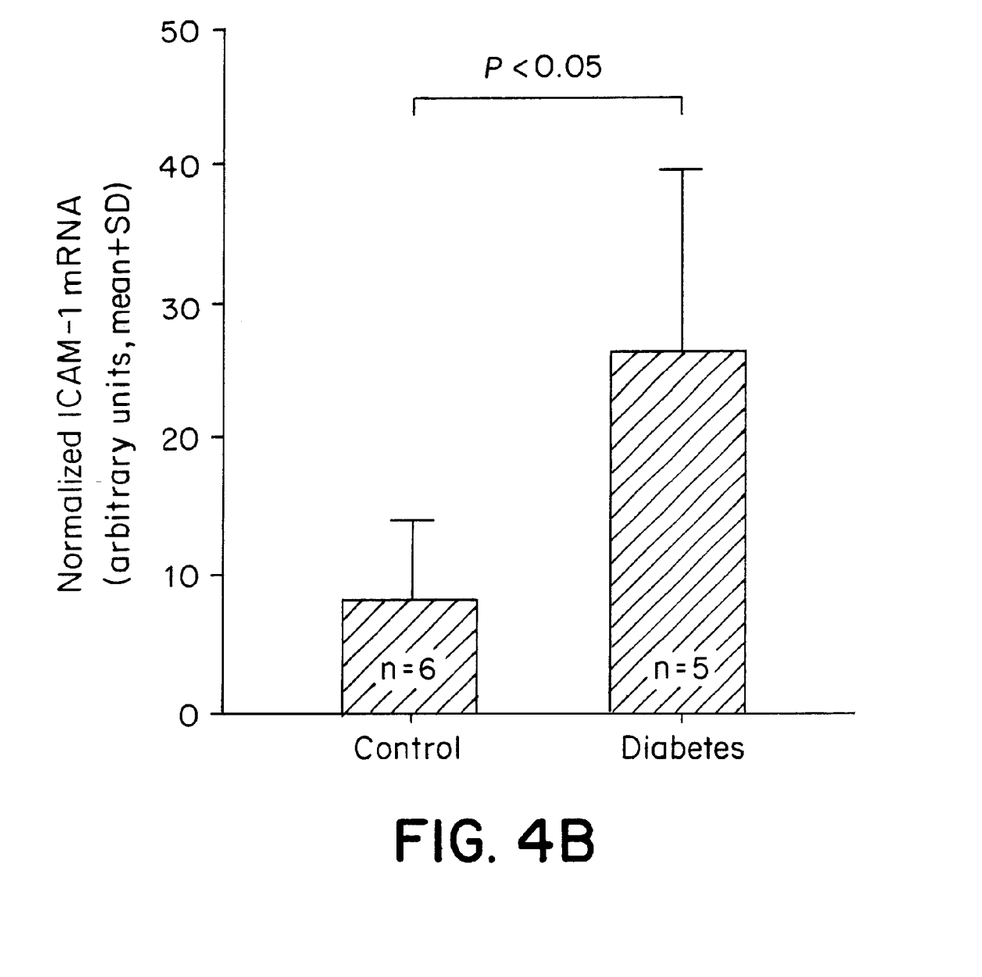
FIG. 4B is a bar graph showing units of normalized ICAM-1 mRNA for controls and seven days after diabetes induction.
Figure 4C:
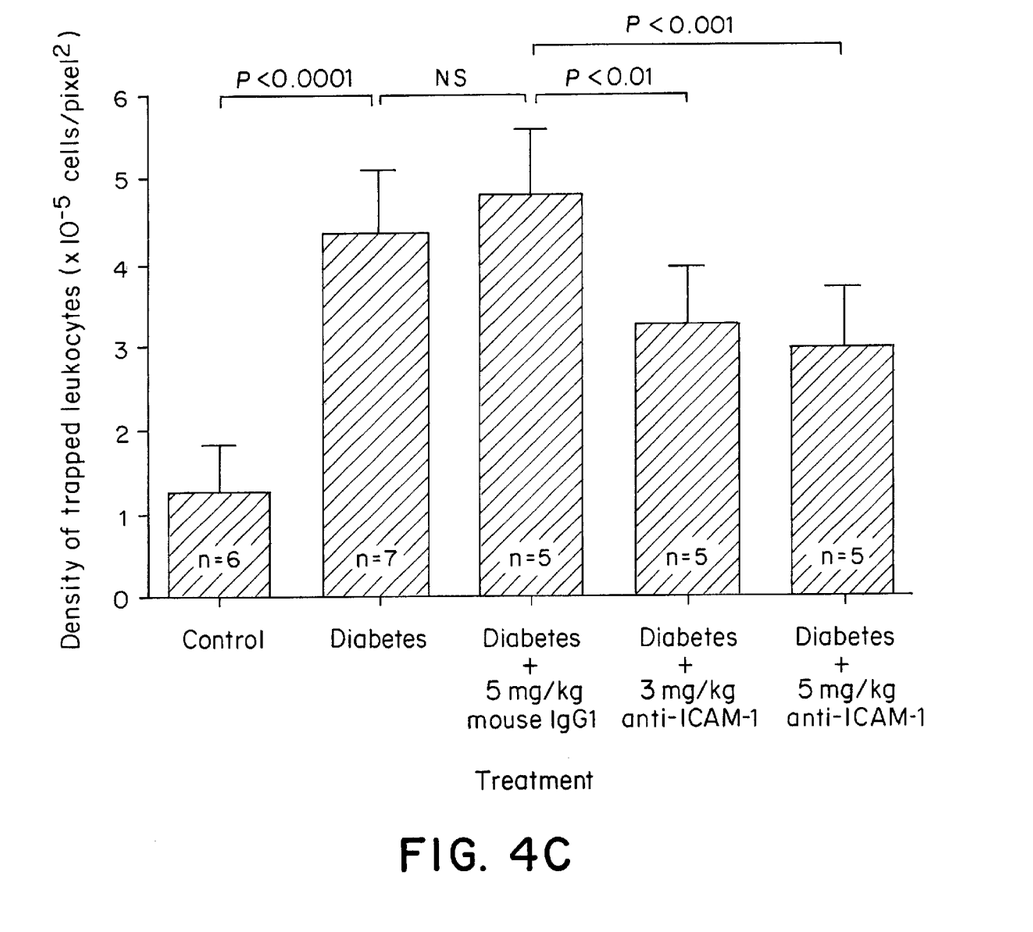
FIG. 4C is a bar graph showing the density of trapped leukocytes ($\times 10^{-5}$ cells/pixel$^2$) for control, diabetic test subjects not given anything, diabetic test subjects given 5 mg/kg mouse IgG1, diabetic test subjects treated with 3 mg/kg anti-ICAM-1 antibody, and diabetic test subjects treated with 5 mg/kg anti-ICAM-1 antibody. NS=Not Significant.

To assess whether ICAM-1 mediates diabetic retinal leukostasis, a well characterized ICAM-1 neutralizing antibody (IA29) was used for in vivo adhesion blockade experiments. Animals received intraperitoneal injections of 3 mg/kg or 5 mg/kg anti-ICAM-1 antibody (# BSA1, R&D Systems, Minneapolis Minn.) or normal mouse IgG (# MAB002, R&D Systems) in sterile phosphate buffered saline three times weekly. ICAM-1 bioactivity is inhibited via systemic administration of the ICAM-1 neutralizing antibody. Animals received either 3 or 5 mg/kg intraperitoneal injections of the ICAM-1 antibody three times weekly. Control diabetic animals received an equivalent amount of a non-immune isotype control antibody. All animals were analyzed one week following diabetes induction. The results showed that the ICAM-1 antibody blocked the diabetes-induced leukostasis by 40.9% (3 mg/kg, n=5, p<0.01) and 48.5% (5 mg/kg, n=5, p<0.001) (FIG. 4C). The peripheral leukocyte counts at one week increased by 40% (5 mg/kg, n=5, p<0.05) compared to the control antibody treated animals, a result consistent with successful systemic ICAM-1 blockade (Table 1). Body weight, plasma glucose and blood pressure were unchanged in all diabetic groups (Table 1). Blood pressure was measured using a noninvasive tail-cuff sensor monitor (Ueda, Tokyo, Japan). Blood anti-coagulated with EDTA was drawn from the abdominal aorta of each rat after the experiment. The blood sample was analyzed using a hematology analyzer.

TABLE 1

Characteristics of control, diabetic, mouse IgG1-treated diabetic, and anti-ICAM-1 mAb-treated diabetic rats

| | Control 6 CR | Diabetes 7 | Diabetes + 5 mg/kg mouse IgG1 5 | Diabetes + anti-ICAM-1 mAb 3 mg/kg 5 | Diabetes + anti-ICAM-1 mAb 5 mg/kg 5 |
|---|---|---|---|---|---|
| n | | | | | |
| Body weight (g) | 271 ± 12 | 240 ± 12* | 235 ± 9* | 238 ± 6* | 239 ± 12* |
| Plasma glucose (mg/dl) | 123 ± 19 | 332 ± 35* | 316 ± 61* | 351 ± 83* | 373 ± 68* |
| Blood pressure (mm Hg) | 111 ± 6 | 104 ± 12 | 109 ± 14 | 105 ± 9 | 105 ± 10 |
| Leukocyte count (x10$^3$/μl) | 6.1 ± 1.6 | 5.0 ± 1.5♦ | 5.3 ± 0.8♦ | 6.9 ± 1.4 | 7.4 ± 2.3 |

Values are means±SD. *P<0.0001 vs. control rats; ♦P<0.05 vs. 5 mg/kg anti-ICAM-1 mAb-treated diabetic rats. All results are expressed as means±SD. Unpaired groups of two were compared using two sample t-test or two sample t-test with Welch's correction. To compare three or more groups, analysis of variance was followed by the post hoc test with Fisher's PLSD procedure. Differences were considered statistically significant when P values were less than 0.05.

Figure 4D:
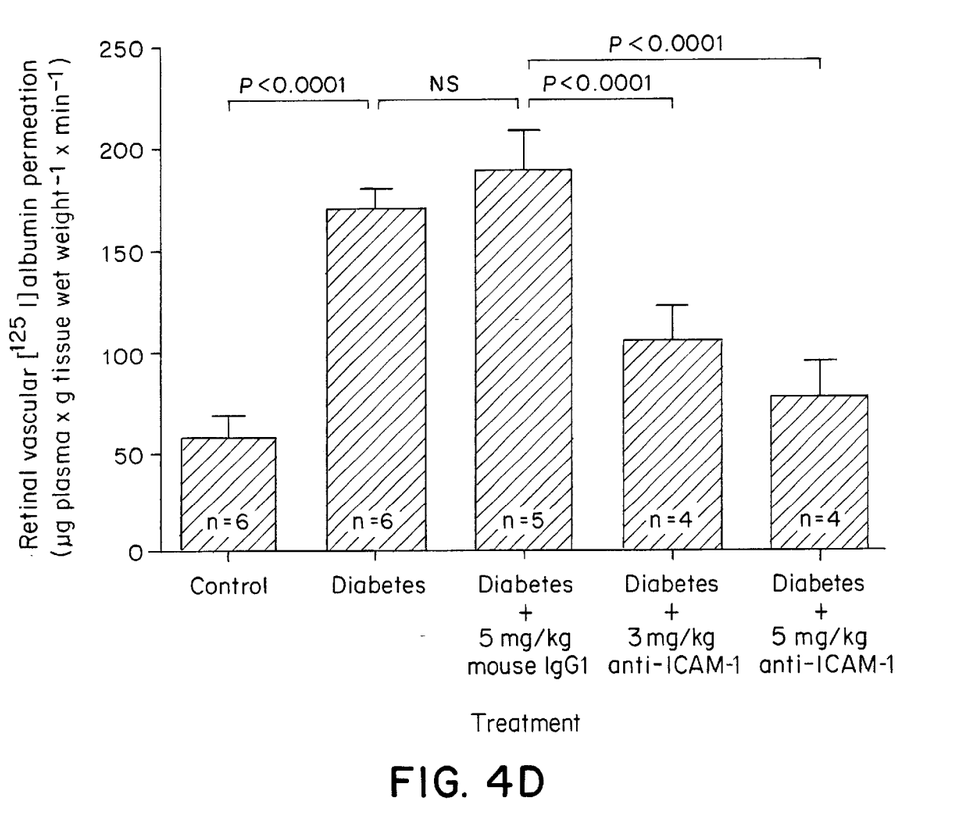
FIG. 4D is a bar graph showing the retinal vascular $^{125}$I albumin permeation ($\mu$g plasma$\times$g tissue wet weight$^{-1}\times$min$^{-1}$) for control, diabetic test subjects not given anything, diabetic test subjects given 5 mg/kg mouse IgG1, diabetic test subjects treated with 3 mg/kg anti-ICAM-1 antibody, and diabetic test subjects treated with 5 mg/kg anti-ICAM-1 antibody. NS=Not Significant.

The effect of the ICAM-1 inhibition on blood retinal barrier breakdown was tested using the same antibody. Animals receiving 3 and 5 mg/kg of the anti-ICAM-1 antibody had 63.5% (3 mg/kg, n=4, p<0.0001) and 85.6% (5 mg/kg, n=4, p<0.0001) less retinal albumin permeation at one week (FIG. 4D). The results suggest that the ICAM-1-dependent component of the leukostasis is largely responsible for blood retinal barrier breakdown.

In summary, these data demonstrate that retinal leukostasis is a very early event in diabetic retinopathy with important, functional consequences. Both early retinal vascular leakage and non-perfusion appear to follow its development. The inhibition of ICAM-1 bioactivity blocks diabetic retinal leukostasis and largely prevents blood retinal barrier breakdown. The inciting stimulus for ICAM-1 upregulation remains unknown, however, it is not likely to be endothelial cell death because ICAM-1 inhibition largely maintains the blood retinal barrier. Taken together, these data identify ICAM-1 as a new therapy for the prevention of diabetic retinopathy and the vision loss it produces.

EQUIVALENTS

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. A method for reducing diabetic retinopathy associated retinal edema and/or retinal ischemia, comprising administering an ICAM-1 antagonist that inhibits the binding of ICAM-1 to LFA-1, wherein the ICAM-1 antagonist is an antisense molecule, an antibody, an antibody fragment, a ribozyme or aptamer; and the ICAM-1 antagonist is administered to the eye, thereby reducing diabetic retinopathy associated retinal edema and/or retinal ischemia.

2. A method for treating an individual having diabetic retinopathy comprising administering an ICAM-1 antagonist, wherein the ICAM-1 antagonist inhibits leukocyte interaction; the ICAM-1 antagonist is an antisense molecule, an antibody, an antibody fragment, a ribozyme or aptamer; and the ICAM-1 antagonist is administered to the eye, thereby treating the individual having diabetic retinopathy.

3. A method for treating an individual with the diabetic retinopathy associated retinal edema comprising administering an ICAM-1 antagonist, wherein a decrease in the retinal edema occurs; the ICAM-1 antagonist is an antisense molecule, an antibody, an antibody fragment, a ribozyme or aptamer; and the ICAM-1 antagonist is administered to the eye, thereby treating the individual with diabetic retinopathy associated retinal edema.

4. A method for treating an individual with the diabetic retinopathy associated retinal ischemia comprising administering an ICAM-1 antagonist, wherein a decrease in ischemia occurs; the ICAM-1 antagonist is an antisense molecule, an antibody, an antibody fragment, a ribozyme or aptamer; and the ICAM-1 antagonist is administered to the eye, thereby treating the individual with diabetic retinopathy associated retinal ischemia.

5. A method for treating diabetic retinopathy associated retinal edema and retinal ischemia comprising administering an ICAM-1 antagonist, wherein a decrease in the diabetic retinopathy associated retinal edema and ischemia occurs; the ICAM-1 antagonist is an antisense molecule, an antibody, an antibody fragment, a ribozyme or aptamer; and the ICAM-1 antagonist is administered to the eye, thereby treating the diabetic retinopathy associated retinal edema and ischemia.

6. A method of treating diabetic retinopathy comprising administering an ICAM-1 antagonist and at least one additional antagonist that inhibits the binding of a leukocyte to an endothelial cell or to another leukocyte, wherein the ICAM-1 antagonist is an antisense molecule, an antibody, an antibody fragment, a ribozyme or aptamer; and the ICAM-1 antagonist is administered to the eye, thereby treating the diabetic retinopathy.

7. The method according to claim 1, wherein a decrease of ischemia occurs.

8. The method according to claim 7, wherein the decrease of ischemia is between about 10% and about 90%.

9. The method according to claim 1, wherein a decrease in edema occurs.

10. The method according to claim 9, wherein the decrease in edema is between about 50% and about 90%.

11. The method according to claim 2, wherein a decrease of ischemia occurs.

12. The method according to claim 11, wherein the decrease of ischemia is between about 10% and about 90%.

13. The method according to claim 2, wherein a decrease in edema occurs.

14. The method according to claim 13, wherein the decrease in edema is between about 50% and about 90%.

15. The method according to claim 3, wherein a decrease in edema occurs.

16. The method according to claim 15, wherein the decrease in edema is between about 50% and about 90%.

17. The method according to claim 4, wherein a decrease of ischemia occurs.

18. The method according to claim 17, wherein the decrease of ischemia is between about 10% and about 90%.

19. The method according to claim 5, wherein a decrease of ischemia occurs.

20. The method according to claim 19, wherein the decrease of ischemia is between about 10% and about 90%.

21. The method according to claim 5, wherein a decrease in edema occurs.

22. The method according to claim 21, wherein the decrease in edema is between about 50% and about 90%.

23. The method of claim 6, wherein the additional antagonist is an integrin antagonist, selectin antagonist, a leukocyte adhesion inducing cytokine antagonist or another adhesion molecule antagonist.

24. The method of claim 23, wherein the integrin is selected from a group consisting of LFA-1, Mac-1, and p150,95.

25. The method of claim 23, wherein the selectin is selected from a group consisting of P-selectin, E-selectin, and L-selectin.

26. The method of claim 23, wherein the cystokine is selected from a group consisting of TNF-1$\alpha$, and IL-1 $\beta$.

27. The method of claim 23, wherein the adhesion molecule antagonist is a VCAM, an ICAM-2 antagonist, an ICAM-3 or another ICAM-1 antagonist.

* * * * *

UNITED STATES PATENT AND TRADEMARK OFFICE
CERTIFICATE OF CORRECTION

PATENT NO. : 6,670,321 B1  Page 1 of 1
APPLICATION NO. : 09/248752
DATED : December 30, 2003
INVENTOR(S) : Anthony P. Adamis It is certified that error appears in the above-identified patent and that said Letters Patent is hereby corrected as shown below:

Please add the following paragraph at Column 1, line 9:

--GOVERNMENT SUPPORT

The invention was supported, in whole or in part, by a grant 2P01 HL32262-15 from the National Institutes of Health. The Government has certain rights in the invention.--

Signed and Sealed this

Twenty-seventh Day of October, 2009

David J. Kappos
*Director of the United States Patent and Trademark Office*